United States Patent [19]

Gontero et al.

[11] Patent Number: 5,520,457
[45] Date of Patent: May 28, 1996

[54] MACHINE AND METHOD FOR THE CONTINUOUS TREATMENT OF SURFACES OF ARTICLES OF REDUCED THICKNESS

[76] Inventors: Roger Gontero, 55 Avenue des Libérateurs, La Vivette; Claude Serra, 2 Impasse du Belier, both of 13080 Luynes, France

[21] Appl. No.: 838,254

[22] PCT Filed: Sep. 25, 1990

[86] PCT No.: PCT/FR90/00684

§ 371 Date: Mar. 10, 1992

§ 102(e) Date: Mar. 10, 1992

[87] PCT Pub. No.: WO91/04679

PCT Pub. Date: Apr. 18, 1991

[30] Foreign Application Priority Data

Sep. 27, 1989 [FR] France .................................. 89 12866

[51] Int. Cl.⁶ .............................. A47J 37/12; A23L 1/18
[52] U.S. Cl. .................... 366/228; 366/233; 366/230; 366/318; 99/423 C; 118/24; 426/289; 15/3.20
[58] Field of Search .................................. 366/219, 220, 366/225, 228, 233, 230, 231, 318; 198/658, 659, 676; 99/404, 423 C; 15/3.20, 3.21, 3.16, 3.19, 3.13; 118/19, 24, DIG. 6; 426/289

[56] References Cited

U.S. PATENT DOCUMENTS

| | | | |
|---|---|---|---|
| 374,102 | 11/1887 | Wiesebrock | 366/225 |
| 967,680 | 8/1910 | Skinner | 15/21.2 |
| 2,308,775 | 1/1943 | Olson | 15/3.21 |
| 2,590,381 | 3/1952 | Currie | 15/3.16 |
| 2,684,206 | 7/1954 | Zettel | 366/220 |
| 3,189,927 | 6/1965 | Dyar | 15/3.16 |
| 3,592,689 | 7/1971 | Chaplinski | 15/3.21 |
| 4,501,499 | 2/1985 | Boan et al. | 366/233 |
| 4,658,708 | 4/1987 | Rastoin | 99/323.9 |

FOREIGN PATENT DOCUMENTS

| | | | |
|---|---|---|---|
| 0192012 | 8/1986 | European Pat. Off. | 99/323.9 |
| 2596956 | 10/1987 | France . | |

OTHER PUBLICATIONS

International Search Report and Annex, in French and English.
International Preliminary Examination Report.

*Primary Examiner*—David Scherbel
*Assistant Examiner*—Reginald L. Alexander
*Attorney, Agent, or Firm*—Greenblum & Bernstein

[57] ABSTRACT

Method and apparatus for the continuous treatment of reduced thickness article surfaces, for example, for the surface treatment of fragile products of small dimensions. The product to be treated is continuously poured, along with a treatment product, if necessary, into a rotary cylinder arranged horizontally or substantially horizontally, and rotated at low speed. A helical brush is also rotated at a reduced speed in an opposite direction to the cylinder, with the brush being arranged parallel to the cylinder and in contact on at least one of its generating lines with at least one internal generating line of the lower portion of the cylinder.

24 Claims, 5 Drawing Sheets

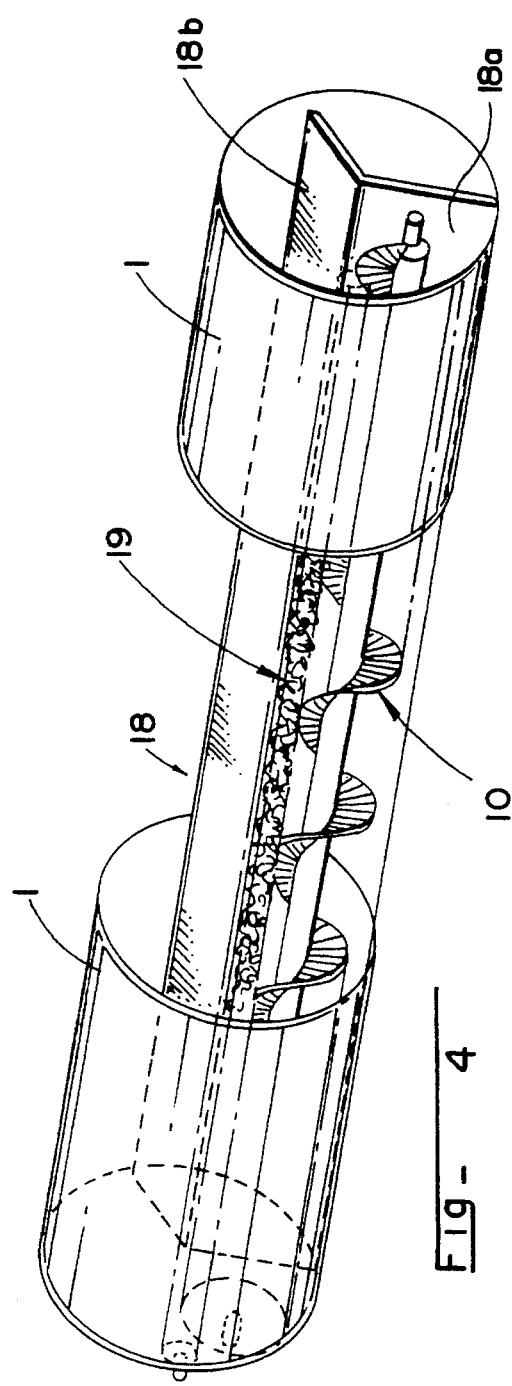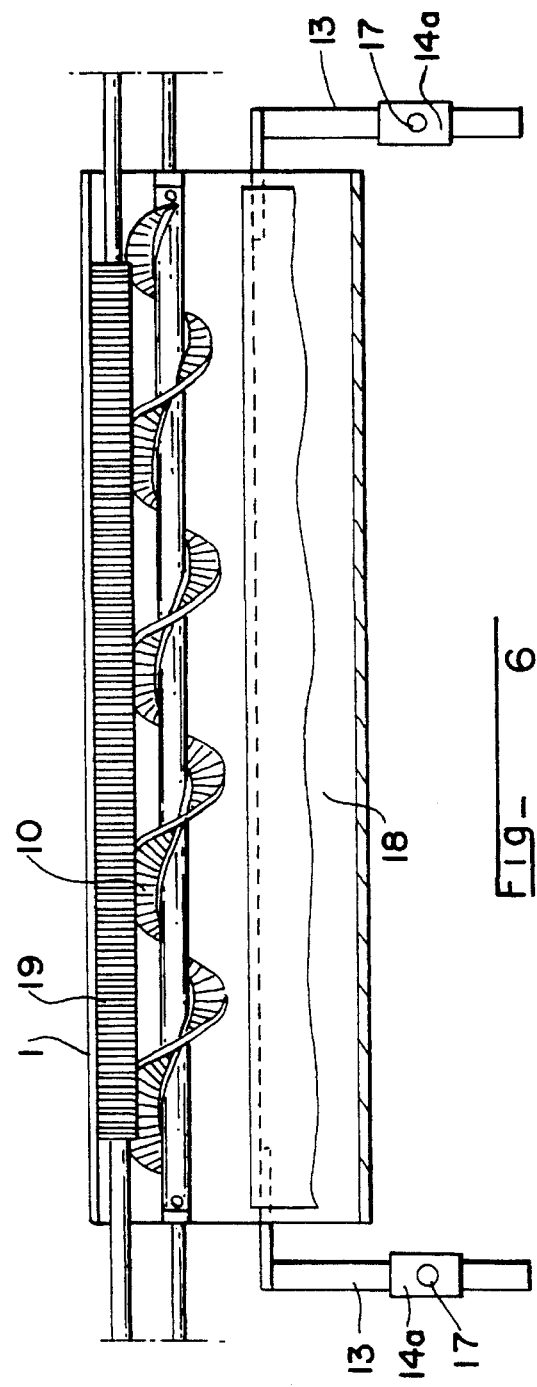

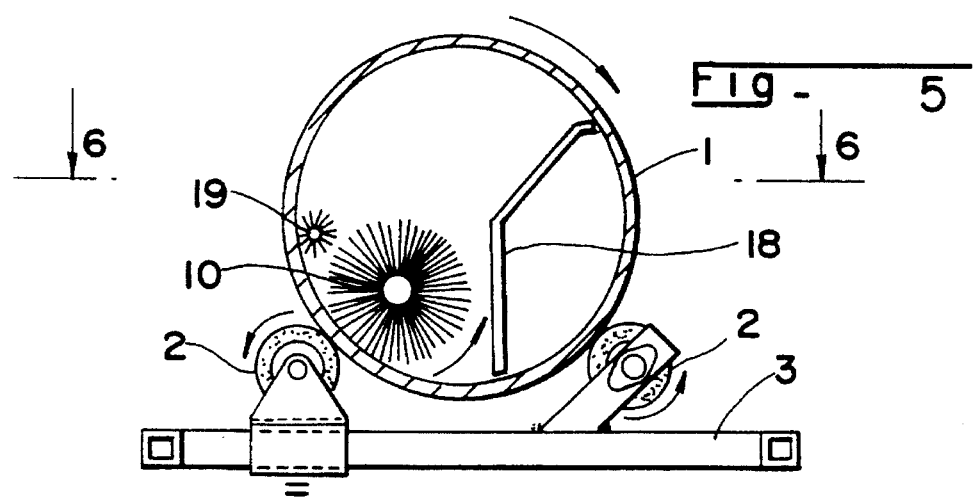
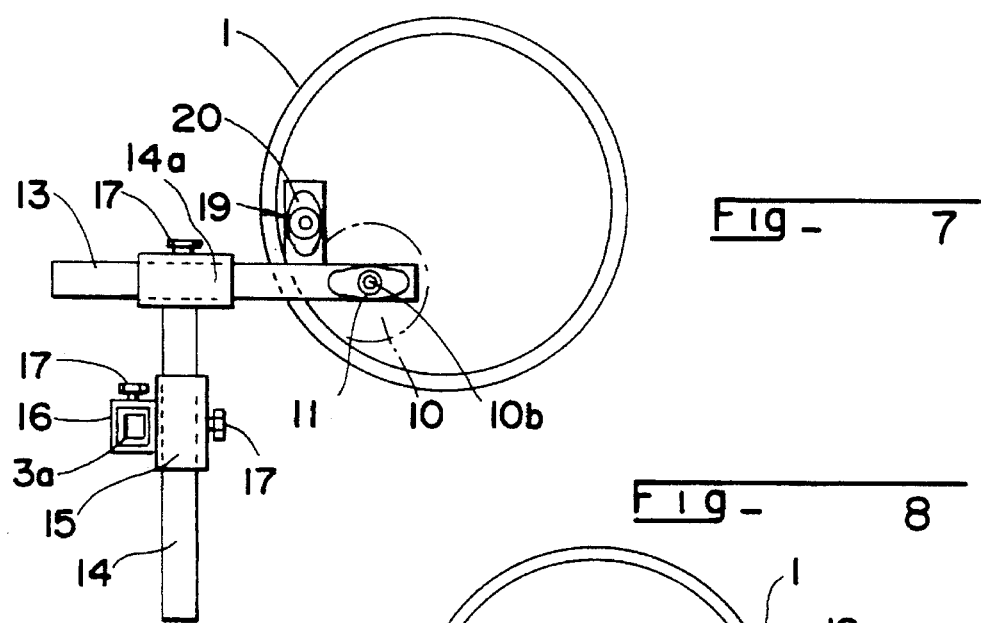
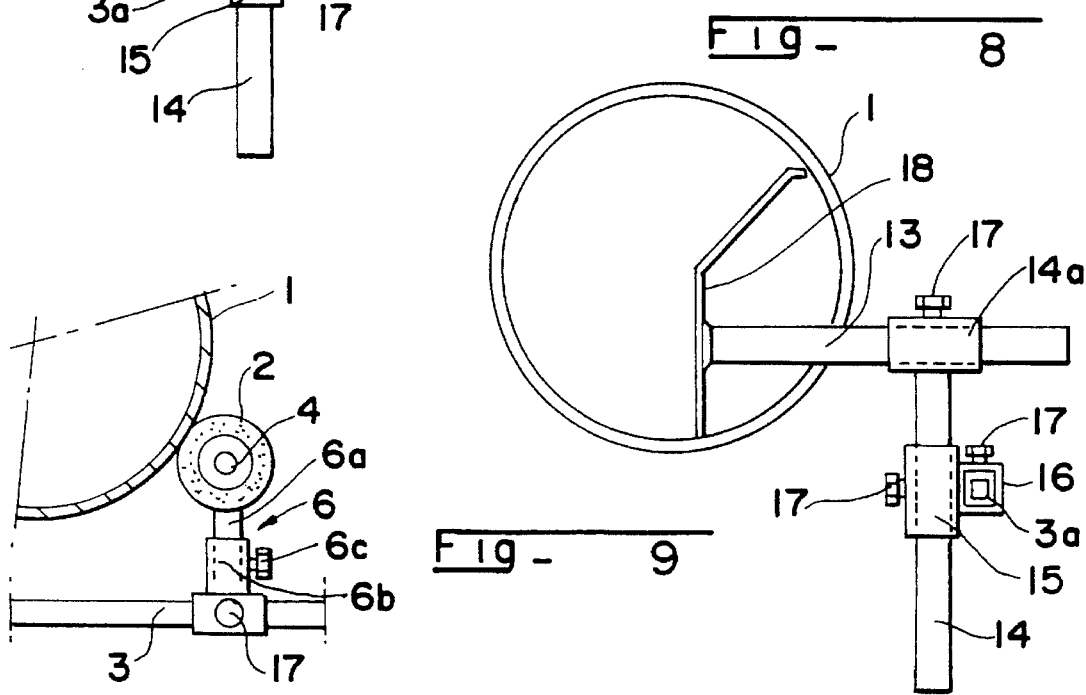

MACHINE AND METHOD FOR THE CONTINUOUS TREATMENT OF SURFACES OF ARTICLES OF REDUCED THICKNESS

BACKGROUND OF THE INVENTION

1. Field of the Invention

The present invention is related to apparatus and method for the continuous treatment of surfaces of articles of reduced thickness, for example for the treatment of fragile products of small dimensions.

2. Discussion of Background Information

The apparatus and method to which the present invention relate can be advantageously applied to the implementation of diverse operations for the treatment of surfaces of small articles, a non-exhaustive list of which follows:

cold or hot coating, with a liquid and/or powdery admixture, of products such as candy and other confectionery goods, cookies, peanuts, dry fruits, grains, flakes of cereals, gelatinized products, extruded products, etc.;

"frosting" candy and other confectionery products (stripping of products coated with sugar-based solution, to stop them from amalgamating together);

"oiling" of peanuts and gelatinized products (application of a thin layer of an oily admixture, to obtain a finished appearance);

"gumming" (depositing a thin layer of gum adapted to retain a powdery product around a solid or compact core, for example to retain salt on certain products, sugar on fruit jellies, dates, etc.; or to maintain the density of brittle products, for example, by depositing a thin layer of gum around a core constituted by a main active agent of pharmaceutical tablets);

hot or cold mixing of products, for example mixtures of dry fruits, grated vegetables, etc.;

applying or removing films from seeds, grains, peanuts, etc.;

"loosening" of products (for example, separation of jellied fruits or other agglutinated products);

sifting and sizing;

brushing or glazing.

The EP-A-0,192,102 discloses an apparatus for uniformly and continuously coating confectionery goods comprising a solid, or gelatinous, or sticky core, coated in liquid and/or powdery products, of the type comprising a substantially horizontal fixed chute, an endless screw which is driven rotationally in the chute, and means to introduce the cores and the liquid and/or powdery products into the chute. The apparatus also comprises at least one helical brush that are formed of bristles implanted radially in a helix on one or two drive shafts that are rotationally driven in the chute at a speed less than 100 revolutions/minute. The chute has the shape of a trough which is opened towards the top, having a height greater than the diameter of the brushes and having a cylindrical base that envelopes the brushes in the portion located beneath the drive shafts.

The performance of such a machine is mediocre. Indeed, the products are pushed in a single direction by the helical brush, and if the products do not have a rounded shape (tablets, round sections of french fries, etc.), these products slide on the wall of the chute instead of turning about themselves, thereby resulting in:

unsatisfactory coating of the products if the machine is used for this function;

inadequate separation of the product units, leading to a choking effect and then a blocking effect that blocks the machine, when the machine is operated in order to implement the "frosting" operation;

a mediocre brushing of the products if the machine is used for this end. To obtain a satisfactory result the chute as well as the helical brush must be extended, and the passage time of the products in the chute must be increased.

On the other hand, when this machine is used to treat viscous, sticky or gluey products, or another product, with a liquid or powdery admixture, the core of the brushes quickly gets excessively encrusted, without any possibility of cleaning these brushes during the functioning of the machine.

FR-A-2,596,956 discloses a machine for the manufacture of coated products, comprising:

a cylinder turning about a substantially horizontal axis whose downstream end is open;

a helical brush with flexible bristles located inside the cylinder, at the upstream end of the cylinder, and which is rotationally affixed to the cylinder;

and a conveyor belt composed of a second helical brush with flexible bristles, which is driven in rotation inside a fixed tube is coaxial with respect to the rotary cylinder which penetrates slightly inside the upstream end of the latter.

The first important disadvantage of this machine is the fact that the rotary cylinder and the helical brush mounted in a fixed manner inside the cylinder turn simultaneously, and in the same direction in such a way that the units or particles of the products are not brushed and agitated from all directions, but are pushed in the direction of the exit by sliding on the internal wall of the cylinder, and this results not only in mediocre agitation and coating, but also in a mass effect due to the accumulation of products which, when they are fragile (pieces of french fries or others), can break and disintegrate. This detrimental phenomenon is accentuated by the presence, inside the cylinder, of radial spacers that rigidly link the cylinder and the axial shaft of the helical brush.

Moreover, the cleaning of such a machine, whose internal surfaces are rapidly covered with deposits resulting from the use of viscous or syrupy products, is very difficult to implement.

SUMMARY OF THE INVENTION

One object of the present invention is thus to overcome disadvantages and inadequacies of coating machines of the type comprising a helical brush housed in a rectilinear conduit arranged horizontally or substantially horizontally.

According to the invention, this aim is achieved by virtue of a process and an apparatus according to which the product to be treated is introduced into a rotary cylinder located horizontally or substantially horizontally and in which at least one rotating helical brush is mounted, the brush turning in an opposite direction with respect to the direction of rotation the cylinder and the brush being in contact, by means of at least one generating line, with at least one internal generating line of the lower portion of the cylinder.

According to another characteristic arrangement, the helical brush has a diameter that is smaller than the internal diameter of the cylinder and is placed in tangential contact with the internal wall of the cylinder.

According to yet another characteristic arrangement, a fixed plate is placed inside the cylinder, in front of the helical brush and parallel or substantially parallel to the helical brush. This plate is separate from the brush and advantageously comprising a lower vertical or substantially vertical portion, and an upper portion arranged obliquely and oriented in the direction of the upper portion of the internal lateral surface of the cylinder.

The invention enables several advantageous results to be obtained. It enables a wide variety of operations in the treatment of surfaces of products with reduced dimensions and of different types, especially of fragile products that disintegrate easily. It yields better results than those that are currently obtained by the implementation of the above-mentioned known materials, due to a better agitation of the products. It reduces the rapidity and the amount of encrustation on the core of the helical brush. It enables automatic cleaning of the internal wall of the cylinder. It also enables the implementation of a wide variety of operations for the treatment of surfaces of diverse products that are presented in the form of units or fragments, introduced continuously and in bulk in the treatment machine.

BRIEF DESCRIPTION OF THE DRAWINGS

The aims, characteristics and advantages mentioned above, as well as others, will become more apparent from the description that follows and from the annexed drawings in which:

FIG. 4 is a perspective and schematic partial sectional view of a variation of the embodiment of the surface treatment machine according to the invention.

FIG. 5 is a transverse sectional view of this machine.

FIG. 6 is a longitudinal sectional view along line 6—6 of FIG. 5.

FIG. 7 is a detailed view showing an embodiment of one of the adjustable-supports of the helical brush.

FIG. 8 is a detailed view showing an embodiment of one of the adjustable supports of the fixed plate.

FIG. 9 is a detailed view illustrating one of the adjustable supports of the rotary cylinder.

DETAILED DESCRIPTION OF THE PREFERRED EMBODIMENTS

Reference will be made to the drawings to describe non-limiting examples of the implementation of the apparatus and the implementation of the method according to the invention.

Figure 1:
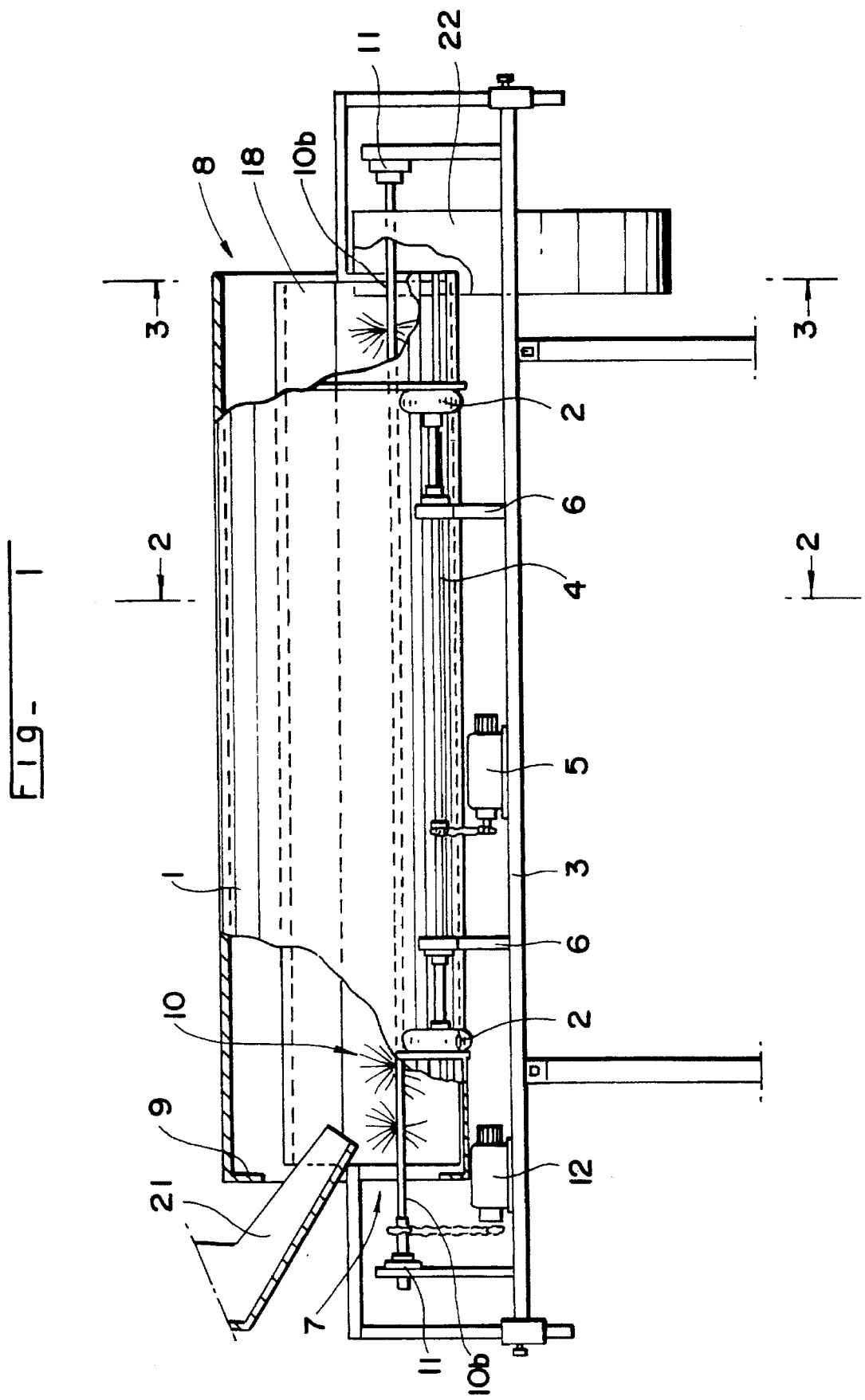
FIG. 1 is a front view, with partial sections, of the surface treatment machine according to the invention.
Figure 2:
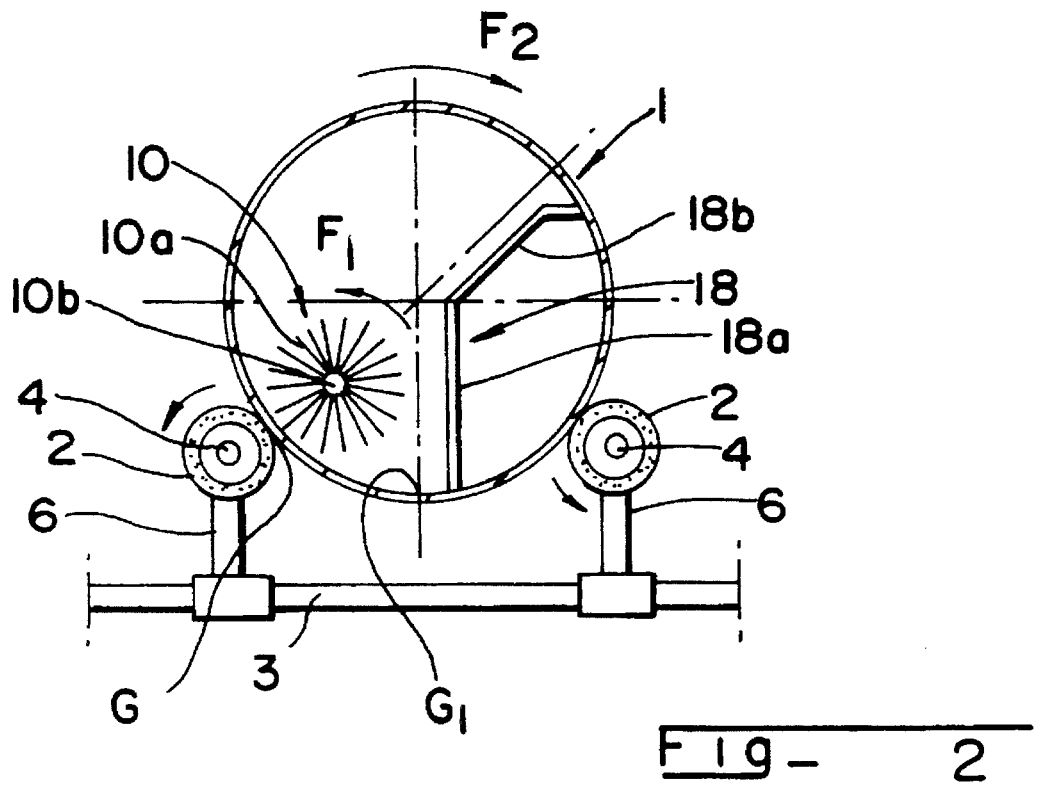
FIG. 2 is a sectional view along line 2—2 of FIG. 1.
Figure 3:
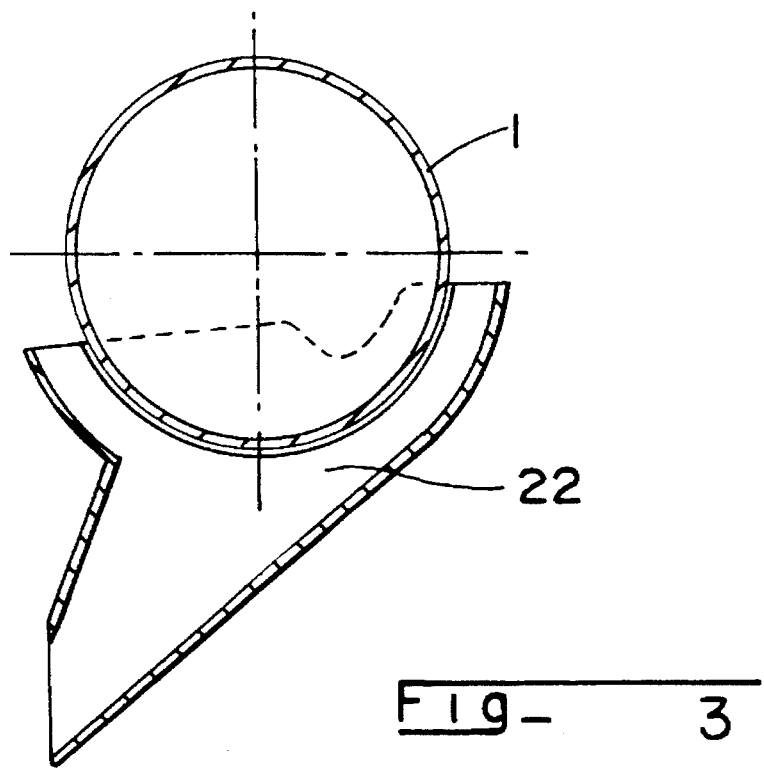
FIG. 3 is a sectional view along line 3—3 of FIG. 1.

According to the embodiment illustrated in FIGS. 1–3, this apparatus comprises a rotary cylinder 1 arranged horizontally or with a reduced inclination. This cylinder is supported by at least two pairs of rollers 2 with a horizontal or substantially horizontal axis.

The rollers 2 arranged on one of the sides of cylinder 1 are wedged on a driving shaft 4 rotationally driven by an electrical motor 5 ensuring, by the intermediary of the shaft and the rollers, the rotational drive of cylinder 1 at a slow and adjustable speed, for example, between 1 revolution/minute and 40 revolutions/minute, according to the nature of the products treated. The link between motor 5 and driving shaft 4 may be ensured by a classic chain and pinion transmission, comprising, moreover, a device for adjusting the tension of the chain.

The bearings of shaft 4 or rollers 2 are carried by vertical supports 6 affixed to frame 3 of the machine.

Cylinder 1 may be advantageously mounted with a limited and adjustable inclination. For this, supports 6 carrying rollers 2 or the bearings of shaft 4, are arranged in a known manner, to enable an adjustment of their height. As illustrated in FIG. 9, supports 6 may, for example, be manufactured in two tubular parts 6a, 6b assembled end-to-end, and equipped with a blocking screw 6c enabling the rigid assembly of these two portions in the desired position. In this way, by inclining the cylinder 1 such that its rear end is raised with respect to its front end, the speed of displacement of the product in the cylinder is reduced, and the duration of the treatment is increased without necessitating an increase in the length of the cylinder.

The ends of cylinder 1 are opened to respectively constitute an entry opening 7 and an exit opening 8. The downstream end demarcating the exit 8 is totally open, whereas the upstream end is partially closed by a shoulder 9 in the form of a circular crown demarcating entry opening 7, and adapted to retain the units or fragments of the treated product which could eventually roll or slide in the direction of the entry opening during introduction of the product into the cylinder.

At least one helical brush 10 is housed in cylinder 1, parallel to the axis of the cylinder, the length of said brush may be just slightly smaller than that of the cylinder. This helical brush is constituted, in a known manner, of flexible bristles 10a, that are, for example, made of a plastic material suited to food products, or of stainless steel, and helically implanted about an axial shaft 10b advantageously made of stainless steel, or a rigid plastic material such as polyamide.

The helical brush 10 may have a single or double mesh and is mounted rotationally in the opposite direction (arrow F1) with respect to the direction of rotation (F2) of cylinder 1. More specifically, cylinder 1 is driven rotationally in the opposite direction with respect to the direction of active rotation of the helical brush, that is, in a direction ensuring the driving of the product in the direction of the downstream end of the cylinder. The ends of shaft 10b, mounted in bearings 11, are carried by vertical elements of frame 3 of the machine, while the rotational drive of the helical brush, at a slow and adjustable speed, for example comprised between 30 revolutions/minute and 100 revolutions/minute is ensured by an electrical motor 12 also installed on the frame, and by means of a transmission, for example, of the chain and pinion type.

The helical brush 10 comes into contact, by means of at least one generating line, with at least one generating line G of the internal surface of the lower portion of cylinder 1.

In a preferred and advantageous manner, the helical brush 10 has nominal diameter that is smaller than the internal diameter of cylinder 1 and it is housed in the lower half-portion of the latter, such that it is placed in tangential contact with at least one generating line G of the internal surface of the lower portion of said cylinder, far from the lowest generating line G1 of the latter (FIG. 2).

The helical brush 10, for example, may have a nominal diameter slightly smaller than the radius of the cylinder 1.

The position of the helical brush 10 with respect to the internal lowest generating line G1 of cylinder 1 is adjustable. To this end, the elements of the frame that support the axial shaft 10b of the helical brush 10 may be made of several parts assembled in an adjustable manner, in a known way, for example by means of sleeves or collars and blocking screws. One embodiment of such adjustable supports is represented succinctly in FIG. 7, bearings 11 of the helical brush 10 carried by a horizontal arm 13 mounted with an ability to slide in a sleeve with a horizontal axis 14a equipping the top of a prop 14 also mounted with sliding latitude in a sleeve with the vertical axis 15 rigidly affixed to a collar 16 which may be displaced along a longitudinal element 3a of frame 3 of the machine. Screws 17 screwed into sleeves 14a, 15 and into collar 16 enable the different elements of the adjustable supports to be immobilized in the desired position.

A plate 18, whose length corresponds substantially to the length of cylinder 1 is arranged longitudinally and in a fixed manner in the cylinder; the length of the plate 18 being, for example, just slightly smaller than that of the cylinder.

This plate 18, that remains fixed during the rotation of the cylinder, is arranged in front of the helical brush 10, at a small distance from the latter and parallelly or substantially parallelly to the brush. It comprises a lower vertical or substantially vertical portion 18a placed in front of the helical brush 10, and an upper portion 18b arranged obliquely and raised in the upper half-portion of the cylinder in the direction of the internal lateral surface of the latter.

A space is arranged between the lower edge of the fixed plate 18 and the lateral surface of cylinder 1, such that the few fragments or units of the treated product that could perhaps fall to the rear of the plate may be brought back in the direction of helical brush 10.

The position of plate 18 may be adjusted by means similar to those that enable the adjustment of helical brush 10. FIG. 8 illustrates an embodiment of an adjustable support, the different elements of which can be compared to the support elements of the adjustable brush represented in FIG. 7, and are designated by the same references.

The devices for adjusting the position of the helical brush 10 and plate 18 enable the brush and the plate also to be placed in an inclined position corresponding to the inclination of cylinder 1 when the cylinder is placed in an inclined position in view of implementing certain treatments.

Figure 10:
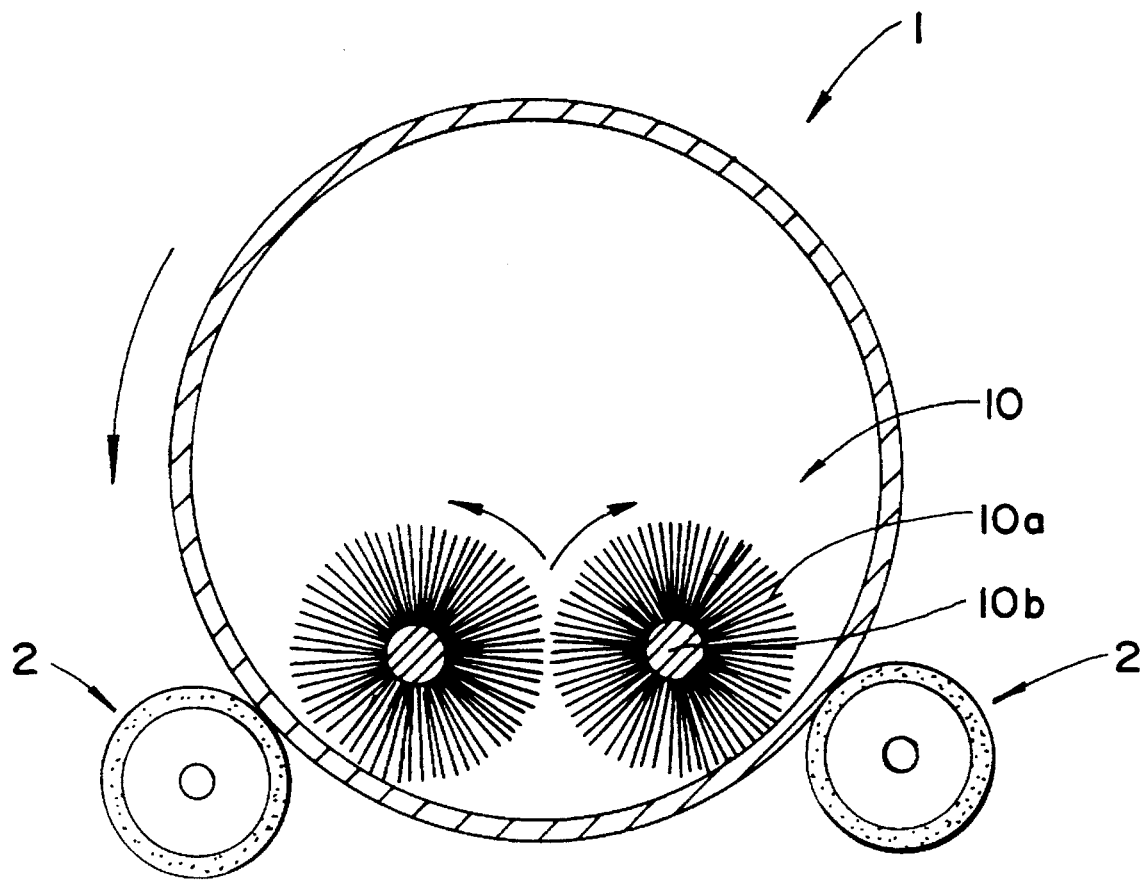
FIG. 10 illustrates an embodiment of the invention including two helical brushes.

According to an embodiment represented in FIG. 10, it is possible to mount two helical brushes inside cylinder 1, the second helical brush also being placed in tangential contact with the internal surface of the lateral wall of the cylinder. In this case, the two brushes are arranged parallelly such that their meshes interpenetrate. They may have diameters that are equal or unequal. Moreover, these two brushes may turn at the same speed or at different speeds.

The brushes are driven rotationally, in opposite directions, by a common electric motor or, each, individually, by its own driving motor, by means of any appropriate transmission system.

FIGS. 4, 5 and 6 illustrate an embodiment that can be compared to the one represented in FIGS. 1–3, but which differs from these basically due to the fact that a cleaning roller 19 constituted by a cylindrical brush, is mounted in parallel to the axis of cylinder 1 and the helical brush 10, preferably in the vicinity of and above the helical brush 10. This cleaning roller is mounted in contact with the internal surface of the lateral wall of cylinder 1, and its function is to maintain this surface completely smooth by removing from it, at all times, any particles that could adhere to it during its operation.

The cleaning roller 19 may be carried by bearings 20 fixed on arms 13 of the adjustable supports of the helical brush 10, so as to enable an adjustment of the position of the roller at the same time as that of the brush.

Below will be described the implementation of the method and the functioning of the apparatus according to the invention.

The solid product to be treated is presented in the form of units (dates, peanuts, etc.) or in small fragments (dried fruits, cereal flakes, etc.) and, according to the nature of the treatment, the powdery product (sugar, salt, etc.) or the liquid product (protective agent, colorant, etc.) for treatment are introduced continuously in cylinder 1, from the upstream end of the latter. The products are, for example, poured in cylinder 1 by means of a chute 21 passing through the entry opening 7 of the cylinder.

The units or fragments of the product and, according to the nature of treatment, the treatment powder and/or liquid that fall to the base of cylinder 1, are driven rotationally by the latter and pushed in the direction of the downstream end of the cylinder by the action of the helical screw 10 placed rotationally in a direction that enables this advance and between whose threads the product is housed. The bristles constituting the helix of the rotary brush, also ensure agitation of the product during its progress in the cylinder. Moreover, the brush tends to push the product back in the direction of the wall of that half-portion of the cylinder that is opposite the half-portion of the cylinder in which it is installed, by considering the vertical median plane of the cylinder. The rotational action of the cylinder, in the inverse direction with respect to the active direction of rotation of the helical brush 10 has the effect of bringing the products back between the threads of the latter. The combined movements of the helical brush and of the cylinder result in the product being returned from every direction, throughout its progress in the cylinder. Plate 18 limits the lateral displacement of the product which the helical brush tends to raise upwardly.

At its exit from the cylinder, the treated product is poured automatically in a receiving container or in a hopper 22 from which point it can be removed or directed to another treatment station, for example by means of a conveyor belt.

We claim:

1. Apparatus for continuous treatment of surfaces of articles of reduced thickness, comprising:

a rotary mounted cylinder;

at least one helical brush comprising radial bristles helically distributed about an axial shaft;

said at least one helical brush being mounted in said cylinder for rotation within said cylinder, with said at least one helical brush being rotatable in a first direction, and said cylinder being rotatable in an opposite direction; and said at least one helical brush includes at least one generating line which contacts at least one internal generating line of a lower portion of said cylinder.

2. The apparatus according to claim 1, wherein said cylinder has an internal wall and an internal diameter, and said at least one helical brush comprises a nominal diameter that is smaller than said internal diameter of said cylinder, and said at least one brush is in tangential contact with the internal wall of said cylinder.

3. The apparatus according to claim 1, wherein said at least one helical brush is positioned in a lower half-portion of said cylinder.

4. The apparatus according to claim 3, wherein said cylinder has an internal wall, and said internal generating line is spaced from a lowermost portion of said internal wall, so that contact between said at least one helical brush and said cylinder is spaced from said lowermost portion.

5. The apparatus according to claim 1, wherein a fixed plate is positioned substantially parallel to said at least one helical brush in said cylinder.

6. The apparatus according to claim 5, wherein said fixed plate comprises a substantially vertical portion positioned in front of said at least one helical brush, and an upper oblique portion oriented in a direction of a lateral portion of an internal wall of said cylinder.

7. The apparatus according to claim 1, wherein said at least one helical brush comprises a second rotary helical brush mounted in said cylinder substantially parallel to a first helical brush, and said second rotary helical brush is rotatable in an opposite direction to said first helical brush.

8. The apparatus according to claim 1, comprising a drive element permitting rotational movement of said cylinder at a slow speed.

9. The apparatus according to claim 8, wherein said drive element permits rotation of said cylinder at a speed between 1 revolution/minute and 40 revolutions/minute.

10. The apparatus according to claim 1, comprising a drive element permitting rotational movement of said at least one helical brush at a slow speed.

11. The apparatus according to claim 10, wherein said drive element permits rotation of said at least one helical brush at a speed between 30 revolutions/minute and 100 revolutions/minute.

12. The apparatus according to claim 1, wherein said cylinder includes an internal wall, and comprising a cleaning roller mounted in contact with said internal wall at a lateral portion of said cylinder.

13. The apparatus according to claim 12, comprising adjustable supports enabling adjustable positioning of at least one of said at least one helical brush and said cleaning roller.

14. The apparatus according to claim 1, comprising adjustable supports enabling adjustable positioning of said at least one helical brush.

15. The apparatus according to claim 5, comprising adjustable supports enabling adjustable positioning of said fixed plate.

16. The apparatus according to claim 5, comprising adjustable supports enabling adjustable positioning of said cylinder so that a downstream end of said cylinder can be raised with respect to an upstream end of said cylinder.

17. The apparatus according to claim 1, wherein said cylinder includes an upstream opening and a downstream opening, and said upstream opening includes baffles for reducing dimensions of said upstream opening.

18. A process for continuous treatment of articles of reduced thickness, comprising:

introducing at least one of articles to be treated and at least one treatment product into a substantially horizontally positioned, rotary cylinder, with the cylinder being rotated at a slow speed;

rotating at slow speed in a direction opposite to the direction of rotation of said cylinder at least one helical brush, said at least one helical brush being arranged within the cylinder and substantially parallel to the cylinder; and the at least one helical brush includes at least one generating line which contacts at least one internal generating line of a lower portion of the cylinder.

19. The process according to claim 18, wherein the at least one helical brush contacts the internal generating line of the cylinder at a positioned spaced from a lowermost portion of the cylinder.

20. The process according to claim 18, wherein the at least one helical brush comprises two helical brushes which are arranged substantially parallel to each other, and one of said two brushes rotates in the same direction as the cylinder and is in tangential contact with a internal surface of the cylinder.

21. The process according to claim 18, wherein the cylinder is rotated at a speed of between 1 revolution/minute and 40 revolutions/minute.

22. The process according to claim 18, wherein the at least one helical brush is rotated at a speed of between 30 revolutions/minute and 100 revolutions/minute.

23. The process according to claim 18, wherein the cylinder is positioned in an inclined orientation, so as to reduce speed of displacement of treated articles, and to increase duration of treatment.

24. The process according to claim 23, including a fixed plate in the cylinder positioned substantially parallel to the at least one helical brush.

* * * * *